(12) United States Patent
Nur et al.

(10) Patent No.: US 8,475,812 B2
(45) Date of Patent: Jul. 2, 2013

(54) GELATIN SPONGE COMPRISING AN ACTIVE INGREDIENT, ITS PREPARATION AND USE

(75) Inventors: Israel Nur, Moshav Timmorim (IL); Eyal Sheetrit, Shoam (IL); Liliana Bar, Rehovot (IL); Guy Tomer, Modiin (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 73 days.

(21) Appl. No.: 12/920,000

(22) PCT Filed: Mar. 2, 2009

(86) PCT No.: PCT/IL2009/000236
§ 371 (c)(1),
(2), (4) Date: Nov. 8, 2010

(87) PCT Pub. No.: WO2009/109963
PCT Pub. Date: Sep. 11, 2009

(65) Prior Publication Data
US 2011/0045034 A1    Feb. 24, 2011

Related U.S. Application Data

(60) Provisional application No. 61/033,174, filed on Mar. 3, 2008.

(30) Foreign Application Priority Data

Mar. 3, 2008 (EP) .................................... 08102227

(51) Int. Cl.
*A61K 9/00* (2006.01)
*A61K 38/00* (2006.01)

(52) U.S. Cl.
USPC ........................................ 424/400; 530/354

(58) Field of Classification Search
None
See application file for complete search history.

(56) References Cited

U.S. PATENT DOCUMENTS

| 2,558,395 | A | 6/1951 | Studer |
| 4,265,233 | A | 5/1981 | Sugitachi et al. |
| 4,292,972 | A | 10/1981 | Pawelchak et al. |
| 4,522,057 | A | 6/1985 | Kerchiss |
| 5,143,838 | A | 9/1992 | Kraus et al. |
| 5,643,596 | A | 7/1997 | Pruss et al. |
| 6,971,813 | B2 * | 12/2005 | Shekalim et al. ............. 401/208 |

FOREIGN PATENT DOCUMENTS

| EP | 0378798 | 7/1990 |
| EP | 0277096 | 7/1992 |
| EP | 0568334 | 11/1993 |
| WO | WO 90/13320 | 11/1990 |
| WO | WO 93/06855 | 4/1993 |
| WO | WO 95/12371 | 5/1995 |
| WO | WO 02/072128 | 9/2002 |
| WO | 2009/109194 | 9/2009 |

OTHER PUBLICATIONS

Streule et al., "PipeJet: A Simple Disposable Dispenser for the Nano- and Microliter Range", Journal of Laboratory Automation, 2004, vol. 9, pp. 300-306.*
International Search Report re: PCT/IL2009/000236 dated Jun. 26, 2009.

* cited by examiner

*Primary Examiner* — Suzanne M Noakes
(74) *Attorney, Agent, or Firm* — David R. Crichton (57) ABSTRACT

The present invention is directed to a method for manufacturing a cross-linked gelatin sponge having a surface by providing a cross-linked gelatin sponge, wetting the surface of the sponge by applying a sufficient amount of liquid comprising a protein or peptide active ingredient, wherein a sufficient amount of liquid is one that retains the flexibility of the sponge even after drying. The sponge is then dried the sponge to obtain a flexible, dry and ready to use cross linked gelatin sponge having a layer of protein or peptide active ingredient on the surface thereof.

15 Claims, 7 Drawing Sheets

GELATIN SPONGE COMPRISING AN ACTIVE INGREDIENT, ITS PREPARATION AND USE

This application is the national stage of application No. PCT/IL2009/000236, filed on Mar. 2, 2009, which application claims priority from U.S. 61/033,174, filed on Mar. 3, 2008. The complete disclosures of the aforementioned related U.S. patent applications are hereby incorporated herein by reference for all purposes.

FIELD OF THE INVENTION

The invention relates to a dry and malleable ready-to-use cross-linked gelatin sponge comprising a layer of active ingredient.

BACKGROUND OF THE INVENTION

Rapid blood loss is particularly difficult to control. Attempts have been made to develop a haemostatic sponge which provides a fast and effective composition for inducing rapid blood coagulation and hemostasis at a wound or bleeding site. One such haemostatic sponge composition is an absorbable gelatin sponge. The spongy physical properties of the gelatin sponge hasten clot formation and provide structural support for the forming clot.

Gelatin sponges are made by foaming a solution of gelatin and drying the foam, usually by lyophilization. Unlike collagen which is naturally insoluble in aqueous solutions, gelatin is soluble at temperatures above 30° C., especially at 37° C.—the body temperature. This characteristic renders the sponge unsuitable for in vivo use as the sponge would dissolve quickly and lose its structural integrity and porous structure. The gelatin must therefore be cross-linked in order to prevent its dissolution in the blood. Methods of cross linking include treatment of the sponge with a chemical cross-linking agent such as formaldehyde, glutaraldehyde, and carbadiimides (e.g. EDC) or treatment of the dry sponge with dry heat (100-160° C. for several hours).

While its mode of action is not fully understood, it is currently believed that its effect appears to be linked to the ability of the gelatin sponge to absorb and hold within its interstices, many times its weight of blood and other fluids. Caught blood platelets interact with the sponge and get activated leading to the formation of a haemostatic plaque and cessation of bleeding. This haemostatic plaque resembles the natural plaque that usually forms after injury. The activated platelets also initiate the coagulation cascade that ends with conversion of soluble fibrinogen into a net of insoluble fibrin by the action of thrombin. Factor XIII which is activated by thrombin in the presence of $Ca^{2+}$ cross-links and stabilizes the clot's fibrin monomers.

GELFOAM and SURGIFOAM Powder are an example of haemostatic devices which can be applied directly to the wounded site with or without thrombin to obtain cession of bleeding. In order to enhance the natural haemostatic property of gelatin, products or kits that combine the haemostatic features of gelatin, thrombin and $Ca^{2+}$ have been developed and manufactured. For example, it is customary that in surgery the gelatin sponge is removed from its package, dipped into diluted thrombin solution and kneaded vigorously until all air is expelled. This step is followed by a second immersion in thrombin solution and application of the wet sponge to the bleeding organ with light pressure. However, the soaking and coating of the sponge requires time-consuming and cumbersome procedures, including freezing, thawing and pre-dilution of the concentrated thrombin solution. Each of the preparation steps introduces potential errors which might compromise the sterile preparation and vary the efficacy of the sponge. Moreover, the complicated procedure requires administration of the sponge by trained emergency personnel. Another major drawback in the pre-wetting technique is that a large volume of liquid is required to fill the sponge voids consequently resulting in low thrombin and $Ca^{2+}$ concentration at the interface between the sponge and the injured site. As a result, the sponges are ineffective in providing and maintaining haemostasis. To overcome this problem, surgeons often resort to the use of high concentrations of thrombin, which can lead to the development of a thrombogenicity risk.

Another problem with certain commercially available gelatin sponges comprising dry thrombin is their lack of flexibility in the dry state. These haemostatic devices do not conform easily to the shape of the body surface to which it is applied. Therefore, it is desired to obtain such all in one ready to use gelatin sponge comprising dry thrombin which easily conforms to the contours of a biological surface, making the manipulation of applying the sponge quicker to perform. Accordingly, blood loss is minimized and valuable surgical time is saved.

U.S. Pat. No. 5,643,596 and WO9512371 disclose an effective haemostatic patch comprising a matrix and at least one haemostatic agent, epsilon aminocaproic acid (EACA) on a single side of a flat patch, namely, the wound-contacting surface. The patch does not contain fibrinogen. According to the description EACA is an important feature, because, surprisingly, it has been discovered that EACA functions as a hemostatic agent in the patch in a manner that approximates the effectiveness of fibrinogen, a coagulation factor. The applicant indicates that surprisingly EACA in the matrix of a patch provides an alkaline environment that accelerates activation of thrombin in comparison with thrombin activation in the absence of EACA. The thrombin can be present in the blood and optionally thrombin provided as an exogenous ingredient of the patch mixed with the alkaline solution in the local environment of the patch. The applicants indicate also that EACA possesses antibacterial properties. A biodegradable matrix, such as absorbable gelatin sponge or calcium alginate, collagen, and oxidized cellulose comprising the EACA on the wound-contacting face of the sponge is disclosed. According to the description, the dry matrix can be applied with or without pre-moistening. According to the description the preferably amount of thrombin that can be applied to the wound-contacting surface is 2-10 $IU/cm^2$. The thrombin component facilitates EACA's adherence to the matrix. The patent application is silent on a biodegradable matrix without EACA.

WO9013320 relates to a dry haemostatic sponge comprising a porous structure of biologically absorbable, solid material containing thrombin, and one or more thrombin-stabilizing agent. The patent discloses several materials for the preparation of the haemostatic sponge, such as collagen, gelatin, chitin, cellulose, polyglycolic acid and polylactic acid. The hemostatic biologically absorbable sponge is prepared by injecting an aqueous solution of thrombin at a multiplicity of sites. The sponge is vacuum dried. According to the description, the injection of thrombin or the extrusion under reduced pressure may result in a sponge that is damaged in key functional/structural characteristics.

U.S. Pat. No. 2,558,395 disclose a ready-to-use gelatin sponge containing thrombin. According to the patent, thrombin is added to an aqueous gelatin solution, transformed into foam and dried in a vacuo at low temperature. The gelatin in this patent was not cross-linked at any stage during the preparation. Thus, upon contact with blood, the gelatin component is dissolved, the thrombin is released immediately and causes the transformation of fibrinogen to fibrin and a fibrin film is formed over the wound.

U.S. Pat. No. 4,292,972 relates to a lyophilized foam sponge product which has a hydrocolloid composition. According to the description the solubility and absorbability of the lyophilized foam product can be reduced by cross-linking either before or after the lyophilization procedure. The lyophilized foam product is formed from a mixture of gelatin, pectin and sodium carboxymethylcellulose.

U.S. Pat. No. 4,265,233 disclose a wound healing material to which thrombin and Factor XIII have been fixed by covalent or ionic bonding. According to the description the wound healing material may be synthetic or naturally polymers. The patent discloses several natural occurring proteins, including Cellulose, viscose rayon, cupraammonium rayon, cellulose acetate, carboxymethyl cellulose, methyl cellulose, agarose, dextran, pullulan, pectin, alginic acid, chitin, polysaccharides such as mucopolysaccharides, and proteins such as wool, silk, collagen, gelatin and casein. The patent does not mention a specific composition of the wound healing material. The examples also disclose that the preparation involves dipping the preformed sponge in an aqueous solution of thrombin and Factor XIII and subsequent freeze-drying for 20 hours.

EP0277096 discloses a hemostatic material, such as GEL-FOAM®, SURGICEL®, and AVICEL®, and collagen which are used in combination with a stabilized thrombin composition. According to the patent the preparation must contain glycols and acetate buffer or phosphate buffer. According to the description the stabilized solution is preferably absorbed onto the hemostatic agent and the pad is freeze-dried and packaged in a sterile manner. In the description it is indicated that Freeze-drying may result in a sponge with low flexibility.

There are also dry fibrin sealant absorbable dressings developed by collaborative efforts between the American Red Cross and the US Army. The dressing consists of two outer layers of human fibrinogen and a middle layer of human calcium chloride and thrombin, freeze-dried onto an absorbable Dexon mesh backing. There are concerns about the durability and friability of the bandage for field use. The dressings are fragile and tend to break apart if not handle carefully. Also, the cost of this dressing is high (Mc Manus and wedmore Business briefing: emergency medicine review 2005).

A dry ready-to-use effective hemostasis dressing for control of hemorrhage, and whose use is easy and does not require any specific training; that is sterile; inexpensive; flexible; and durable is a long felt need. Particularly, there is a need for the development of an "all in one" ready-to-use gelatin sponge that contains highly concentrated and thin layer of an active protein/peptide active compound, such as thrombin, on the sponge surface that adheres to the wound and which maintains the original key structural characteristics such as height, texture and appearance of the gelatin sponge.

SUMMARY OF THE INVENTION

In one aspect, the invention provides a method for manufacturing a cross-linked gelatin sponge having a surface comprising: a) providing a cross-linked gelatin sponge, b) wetting the surface of the sponge by applying a sufficient amount of liquid comprising a protein or peptide active ingredient, wherein a sufficient amount of liquid is one that allows substantially retaining the flexibility of the sponge after drying, and c) drying the sponge, thereby obtaining a flexible, dry and ready to use cross linked gelatin sponge comprising a layer of protein or peptide active ingredient on the surface of the sponge.

In one embodiment of the present invention, the ready to use sponge retains at least 75% of the thickness of the sponge provided in a).

In a further embodiment of the invention, the layer comprising the active ingredients is equal or less than 24% of the overall thickness of the ready to use sponge.

The drying procedure can be carried out in a vacuum oven or by freeze drying, or by any other method known to the skilled person.

The active ingredient applied to the cross linked gelatin sponge of the invention can comprise thrombin. It is desirable that the thrombin activity in the layer of the ready to use sponge is in the range of about 1 to about 300 IU/cm$^2$, or in the range of about 10 to about 40 IU/cm$^2$, in particular in the range of about 20 to about 40 IU/cm$^2$.

Another object of the invention is to provide a ready-to-use cross linked gelatin sponge obtainable according to the invention.

Another aspect of the invention relates to a flexible, dry, and ready-to-use cross-linked gelatin sponge comprising a layer of a protein or peptide active ingredient on only one surface of the sponge, wherein the average thickness of said layer is not more than about 20% of the overall thickness of the ready to use sponge, the majority of the protein/peptide content in said layer is discrete.

In one embodiment of the invention, the active ingredient comprises thrombin. In a further embodiment of the invention, the thrombin activity is in the range of about 1 to about 300 IU/cm$^2$, or in the range of about 10 to about 40 IU/cm$^2$, in particular in the range of about 20 to about 40 IU/cm$^2$.

The ready-to-use cross-linked gelatin sponge according to the invention can be used in medicine. In another embodiment of the invention, the ready-to-use cross-linked gelatin sponge can be used for haemostasis. In another further embodiment of the invention, the ready-to-use cross-linked gelatin sponge can be used in kidney hemorrhage.

One object of the present invention is to provide a package containing a sterile ready-to-use cross-linked gelatin sponge according to the invention.

Another object of the present invention is to provide a method for arresting bleeding at a bleeding site, comprising administering to a bleeding site a ready-to-use cross-linked gelatin sponge according to the invention or a package according to the invention.

The cross-linked gelatin sponge obtainable according to the invention can be used for the manufacturing of a medicament for arresting bleeding.

BRIEF DESCRIPTION OF THE DRAWINGS

The features, aspects, and advantages of the present invention will become better understood with regard to the following description, examples, claims, and the following figures.

DESCRIPTION OF EMBODIMENTS OF THE INVENTION

In one aspect, the invention provides a method for manufacturing a dry and malleable ready-to-use cross-linked gelatin sponge comprising a layer of protein or peptide active ingredient on the surface of the sponge.

Results obtained according to the invention show the advantages of a haemostatic gelatin sponge obtained by a method comprising a) providing a cross-linked gelatin sponge, b) wetting the surface of the sponge by applying a sufficient amount of liquid comprising a protein or peptide active ingredient, wherein a sufficient amount of liquid is one that allows substantially retaining the flexibility of the sponge after drying, and c) drying the sponge, thereby obtaining a flexible, dry and ready to use cross linked gelatin sponge comprising a layer of protein or peptide active ingredient on the surface of the sponge.

For example, it was found according to the invention using various sources of cross-linked gelatin sponges (e.g. Spongostan™, Gelitaspon™, and in-house prepared gelatin sponge) that: wetting the sponge with increasing levels of liquid followed by vacuum drying significantly affects the thickness of the sponge. In fact, the levels of liquid uptake were shown to be inversely proportional to the sponge thickness in the dried sponge. For example, increasing the amount of liquid used for the application of the layer of active ingredient by using a wetting agent such as 0.01 and 0.1% NP40, 20% ethanol (in an amount that does not affect thrombin clotting activity), and 0.02% Tween 20, subsequently lead to an overall decrease in the sponge thickness in the dried sponge. This decrease in thickness of the sponge reflects damaged integrity and porosity of the sponge. It was also found that this damage affected the ability of the sponge to absorb water, i.e., thinner sponges, obtained by drying wetted sponges with increased levels of liquid which were applied to one side of the sponge, absorbed less water than the original non wetted sponges. Of note, according to the US Pharmacopeia absorbable gelatin sponges should absorb not less than 35 times their weight of water. We found according to the invention that in order to meet the pharmacopeia demand, a gelatin sponge such as SPONGOSTAN™ having an initial thickness of 10 mm should retain a thickness of equal or more than 7.44 mm, after wetting and drying i.e. loss of thickness after wetting and drying the gelatin sponge should be not more than 25% from their initial height.

It was also found according to the present invention that drying method by, lyophilization or vacuum drying procedure, both being methods which are currently used and are appropriate for use with protein/peptide ingredients can affect the thickness layer of the active ingredient within the Sponge. The findings show that an increase in the net liquid uptake resulted in a decrease in overall thickness of the sponge in a similar extent in both lyophilization and vacuum drying procedure. However, when comparing the thickness of the layer of the applied active ingredient within the sponge, the results show that drying in vacuum results in a thinner layer of active ingredient as compared to the lyophilization drying procedure. For instance, the dried top layer (or layer of the applied active ingredients) of the vacuum dried sponge was 5.8-8.3% of the overall thickness of the sponge as compared to 12.5-24% in the lyophilized sponge. The findings according to the invention also show that a dry sponge subjected to complete soaking followed by lyophilization is by far less flexible (shows a dry cookie structure) than a sponge subjected to partial soaking and dried by vacuum oven, and therefore the latter is more malleable. When thrombin was used as the active ingredient, the thrombin was released faster in the sponge prepared using complete soaking and dried by lyophilization than in a sponge prepared by partial soaked sponge and dried in a vacuum oven in which in the thrombin was gradually released. Whereas, at the end of the testing both sponges had similar recovered activity indicating that the partial soaked sponge dried in a vacuum oven preserves the thrombin activity.

The results obtained indicate that for obtaining a sponge with a thinner layer of active ingredient and/or having the ability to slow release of the active material the vacuum drying procedure can be used. For obtaining a sponge with thicker layer of active ingredient the method of drying by lyophilization can be used. However, vacuum drying procedure may be desired instead of lyophilization drying procedure when taking into account the following advantages of vacuum drying procedure: cheap manufacturing, shorter preparation time and substantially preservation of the original porous structure and mechanical properties of the sponge.

The flexibility of the sponge post drying procedure can be measured by any method known to the skilled person. For example, by the three point flexural test using a Texture analyzer, such as LLOYD NEXYGEN LF plus 01/LFLS/LXA/EU.

More specifically, it was found according to the invention that a pre-made gelatin dry sponge prepared with a 2.5×2.5×1 cm sponge that absorbed a small volume of liquid like up to about 220 μl when coated with the active ingredient and thus only a relative thin layer of that sponge is wetted while the bulk of the sponge remains dry is a pre-made sponge substantially unchanged in its structure compared to the basic uncoated sponge. This sponge contains a relatively thin dry layer of active ingredient on its wound facing side. This layer, which can be easily distinguished from the non-biology side of the sponge, is less porous in appearance than other non-treated faces of the sponge. This layer is stable and the layer comprising the active ingredient is discrete upon storage, but when wetted the active ingredient dissolves and diffuses out. The term "discrete" refers to a layer which does not undergo flaking.

When the initial thickness of the gelatin sponge is 10 mm, the overall thickness of the dry ready to use sponge can be in the range of about 7 to 9.8 mm, such as about 7.3, 7.44, 7.5, 8, 8.2, 8.5, 9, and 9.5 mm, i.e. 70 to 98%, such as 73, 74, 75, 80, 82, 85, 90 and 95% of the original un-coated gelatin sponge.

Examples of proteins or peptides active ingredients include, but are not limited to, thrombin, proteolytic enzyme obtainable from snake venom, fibrinogen, vitamin k-dependent-clotting factors, factor XIII, RGD peptides, fibronectin, vonWillebrand, growth factors such as platelet derived growth factors, cartilage inducing factors, osteoid inducing factors, bone growth factors, collagen growth factors, cytokines, hormones, and combinations thereof. It is desirable that the proteins or peptides active ingredients substantially retain their activity following the drying procedure.

One or more of the following are advantages of the sponge made according to the invention: maintain of malleability, flexiblility, original texture, intactness of majority of porous structure of the original non-coated sponge, the active ingredient is highly concentrated as a thin layer at the interface of the wound, pre-wetting is not required before use allowing direct application.

The method of manufacture of the sponge of the invention can be scaled to an automatic machine, and can be affected by vacuum drying which is typically of lower cost.

The ready-to-use gelatin sponge can be used as a wound healing sponge. In such an embodiment, the sponge can be coated with various proteases such as hyaluronidase or collagenase or with various combinations of specific protease inhibitors for treating non healing ulcer or facilitate the regrowth of skin.

These proteins can be isolated from plasma of human beings or mammals or can be recombinant. The amount of protein in the layer can vary from very low to above saturation. According to the invention, a colloidal solution can be applied to the surface of the sponge.

Haemostatic characteristics of the gelatin sponges prepared by partial soaking with a thrombin solution and drying by using a vacuum oven were tested in the in vivo Rat Kidney Hemorrhage Model as described in the example methods. The results according to the invention show that the sponge prepared according to the method of the invention was equally efficient in preventing blood loss when applied to a bleeding surface as the fully soaked sponge but was more malleable.

The findings show that a ready-to-use gelatin sponge prepared by the method of the invention is very efficient to stop bleeding in the animal model of Kidney Hemorrhage. For example, it was found that a sponge of the invention prepared by application of a total amount of thrombin applied to the wound-contacting surface of the sponge of 35 IU/cm$^2$ thrombin and further subjected to vacuum drying was at least 3 times more effective in stopping blood loss than the control sponge lacking thrombin. Thus, the thrombin activity in the layer of the ready to use sponge can be in the range of about 1 to about 300 IU/cm$^2$ such as in the range of about 10 to about 40 IU/cm$^2$ or in the range of about 20 to about 40 IU/cm$^2$, or about 35 IU/cm$^2$ thrombin.

The liquid comprising the active ingredient can be applied by any method known in the art. Examples for applying the active ingredient include, but are not limited to, passive application by capillary force or active application by spraying the thrombin liquid on the sponge or pressing the sponge against a thrombin-saturated roller. In one embodiment of the invention, the wetting is by passive capillary force. The liquid comprising the active ingredient can be any aqueous liquid suitable for carrying the active ingredient and/or for administering into the body. In one of the embodiments of the invention, the liquid is L9 (20 mM sodium acetate, 0.5% w/w human albumin, 2% w/w mannitol at pH 6.9-7.1)+saline.

The ready to use sponge can be supplied in a sealed sterile package, such as aluminum foil pouch, which enables removal of the patch without contamination.

Any sterilization method known in the art that does not degrade the biological compounds which are sensitive to thermal procedures can be used including, but not limited to, electron beam irradiation, gamma irradiation. In one embodiment of the invention, the ready to use sponge and packaging material are sterilized together using, for example, gamma radiation.

The component of the ready to use haemostatic sponge can be activated upon application to the desired site to form a clot by the endogenous blood.

The ready to use sponge can be applied and held under pressure onto the desired site for a period of time sufficient for clotting to occur at the interface between the sponge and the application site and for bleeding to be substantially ceased.

The haemostatic ready-to-use gelatin sponge can be prepared from a self manufactured gelatin sponge, e.g. as described in the examples, or by using various commercial sponges such as, for example, Spongostan™, Gelitaspon™.

The haemostatic sponge of the invention can be prepared and provided in a variety of sizes and shapes, depending on the intended use. For example, the haemostatic device of the invention can be prepared using the following sponge sizes: 8×ø3 cm, 10×10×1 cm, 1×1×1 cm, 7×5×1 cm, 2.5×2.5×1 cm.

The sponge of the invention can be spherically, conically, cubically, cylindrically or cut into small squares.

The sponge according to the invention can be provided in a kit form comprising any of the above described haemostatic sponges. The kit can comprise numerous ready to use sponges. The kit can comprise a sterilized surgical instrument for example, scalpel, hemostat and/or instruction for use. The kit can further include a sterile saline solution.

In one embodiment of the invention, the ready to use haemostatic sponge provides effective haemostasis for rapid control of bleeding, including severe or brisk bleeding.

As used herein "severe or brisk bleeding" refers to cases of bleeding where high volumes and high rate of bleeding occurs. Examples of sever and brisk bleeding include, but not limited to, bleeding due to arterial puncture, liver resection, kidney resection, hemophiliacs and patient receiving anticoagulant medication and the like.

A ready to use sponge or kit according to the invention can be advantageously used in several clinical setting including as a homeostatic agent and/or as an anti-adhesive agent and/or for repairing and/or treating injured tissue. As such the sponge and kit can be beneficial in reconstructive and cosmetic surgery of tissues, including cartilage, nerve and bone regeneration.

The term haemostatic agent refers to the ability of the agent to stop the bleeding from an injured blood vessel and/or to contribute to keeping the blood contained within the blood vessel. The bleeding can occur as a result of surgical procedures, haemostatic disorder or in other situations where bleeding must be stopped, for example, in patients with coagulopathies or who are receiving heparin or anticoagulants. In one embodiment of the invention, the gelatin sponge is in close contact with the bleeding tissue.

Adhesion formation is an undesired side-effect in which body tissues that are normally separated grow together. This undesirable side-effect can occur as a result of surgical procedures or non-surgical insults such as endometriosis, infection, trauma, chemotherapy, radiation and cancer. Typically, anti-adhesive agents refer to agents capable of forming a physical barrier (coating) separating between adjacent tissues at the surgical site and therefore preventing and/or reducing formation of post-operative adhesions.

The concentration of the thrombin in sponge and the kit of the invention are preferably selected to optimize the efficacy and functionality of the protein. It is to be noted, however, that varying the thrombin concentration may be done to vary the viscosity and the polymerization time of the combined components.

The amounts and concentrations can be determined empirically by any method known to the skilled person. For example, thrombin activity can be determined directly, by the modified, European Pharmacopeia Assay (0903/1997) procedure, the clotting time is calculated automatically by a clotting machine and the activity is interpolated from a calibration curve prepared using an appropriate thrombin standard, and/or indirectly, by measuring migration length on a slanted surface (or drop test model), or by any other method known to the skilled person.

Other than said thrombin, the sponge and kit of the invention may contain substances which encourage the formation of the clot, such as $Ca^{2+}$, Factor XIII, Factor VIII, fibronectin, vitronectin, von Willebrand factor (vWF).

The ready to use sponge can comprise agents which facilitate the wetting of the sponge or reduce the hydration time of the sponge when administered to a subject in need. The surfactant can be incorporated into gelatin solution prior to foaming, applied to the surface of the cross-linked gelatin sponge, or included in the liquid comprising the active ingredient. Non limiting examples of suitable surfactant include, but are not limited to, Tween 20, ethanol, NP 40.

The sponge can further comprise one or more active ingredient protein or peptide and serve as a drug delivery system.

The term active ingredient protein or peptide is used herein to refer generally to an ingredient suitable for administration to a patient and that induces a desired effect. The term includes ingredients that are therapeutically effective as well as prophylactically effective. Non limiting examples of active ingredients proteins or peptides are therapeutic agents (such as antimicrobial agents, anti-inflammatories), anti-cancer drugs, chemotherapy agents, analgesics, enzymes, hormones, bone morphogenetic proteins, minerals, cartilage inducing factors, growth factors, molecules which stimulate cell migration, adhesion and/or proliferation and the like.

The term drug delivery system refers to delivery of active proteins or peptides which are incorporated into the sponge allowing a controlled delivery of the protein or peptide in a specific tissue in vivo.

The disclosure of ranges in the description of the invention is easily understood by the skilled person. It means the disclosure of continuous values and figures between the limits of the ranges, including the limiting figures and values with all combinations of intermediate sub ranges.

The disclosure of applications, patents and publications, cited above or below, is hereby incorporated by reference.

The following examples are illustrative but not limiting.

EXAMPLES

Methods

Lyophilization Drying Procedure. The lyophilization procedure was carried out as follows using the CHRIST, EPSILON 2-8D Freeze Dryer: The shelves temperature was lowered to −45° C. for 2 hours. Afterwards, the temperature was lowered to −50° C. for an additional 30 minutes. Then the shelves were kept at −50° C. for a period of 5 hours. This step was followed by sublimation at −15° C. and 0.14 mbar for up to 24 hours. After that the shelves temperature was increased to +25° C., pressure was reduced to 0.02 mbar and secondary drying was carried out for up to 24 hours.

Vacuum Drying Procedure. Vacuum drying procedure was done in an oven (ShelLaB Model 1430-2E) set to room temperature at a pressure of 0.1 bars or less for 3 to 4 hours.

Production of Gelatin Sponge (In house Sponge). 30 g gelatin flakes (PB Gelatins; Pharmaceutical gelatin, Type A from pig skin, 250 Bloom, 8 mesh; Cat. No. 1154) were added to 500 ml distilled water. The dispersion was heated to 50-60° C. until the gelatin was completely dissolved. The solution (6% w/v) was then cooled to 50° C. and transferred to a mixer bowl (KitchenAid Heavy Duty Model 565SS) where it was whipped for about 2 minutes until a stable foam was formed which had a 6-8 fold higher volume compared to the initial volume of the gelatin solution. The foam was poured into a metal mold (21×30 cm with a depth of 1.5 cm). In order to harden the foam, the mold was placed at 4° C. for 1 hour. Afterwards, the mold was transferred to a lyophilizer with pre-cooled shelves (4° C.). The lyophilization drying procedure was carried out as described above. Following the drying procedure, the dry sponge was cross-linked by heating at 160° C. for 3 hours at atmospheric pressure.

Thrombin Release from the Sponges. The sponges (2.5× 2.5×1 cm) were immersed in 10 ml buffer (0.4% Tri-sodium citrate dehydrate, 154 mM NaCl and 1% BSA) inside a 50 ml polypropylene tube which was placed on a roller at room-temperature.

Thrombin release from the sponges was measured by determining the recovered thrombin activity in the various time points according to the following modified, European Pharmacopeia Assay (0903/1997), procedure. Briefly, each standard solution of thrombin (4, 6, 8 and 10 IU/ml; Omrix IL; prepared as described in U.S. Pat. No. 5,143,838 and in EP patent 378,798) was incubated for 2 minutes at 30'C. Then 40 ml thrombin solution of each standard solution was mixed with 160 µl fibrinogen solution (0.1%; Enzyme research Laboratories; cat No FIB1) and clotting time was measured (Haemostaisi analyser: Diagnostica Stago; Model Start). A calibration curve of log clotting times vs. log thrombin concentration was plotted. 0.3 ml samples were taken out from the tube out of which 40 µl were used for the measurement (the same amount of buffer was added back to replace the sample volume). The measurements were carried out in duplicates in the following time points 2, 5, 10, 15, 30, 45 and 60 min after the beginning of the experiment. Thrombin activity was determined by the clotting time obtained (calculated automatically by a clotting machine, interpolated from the calibration curve and multiplied by the dilution factor).

Rat kidney hemorrhage model. Sprague Dawley albino rats, weighing 350-500 g were housed in an authorized facility according to the current ethical requirements. The health of each animal was ascertained and only overtly healthy animals were used for testing. Following receipt, the animals were subjected to an acclimation period of at least 5 days. The animals were provided ad libitum a commercial rodent diet and free access to drinking water. The animal was anesthetized with an intraperitoneal injection of Pental (30-50 mg/kg).

Afterwards, the animal's fur was shaved on the left flank for the paralumbar laparotomy. The shaved site was wiped with alcohol. To maintain a temperature of 38-40° C., the rat was placed on a plastic cover deck on top of a water bath preheated to 40° C. A thermo probe was inserted into the animal's rectum and the body temperature was monitored. The animal was positioned laterally and Sodium Heparin (2000 IU/Kg) was injected intravenously through the tail vein. A left paralumbar incision was made from the left hip to the twelfth rib, and the left kidney was exposed and separated from the perirenal fat. The rat was re-positioned to dorsal recumbence and allowed to stabilize for a period of five minutes or until the body temperature was utmost 39° C. The renal vessels were occluded with a soft vascular clamp and a gauze pad was tucked into the dorsal edge of the incision, between the exteriorized kidney and the incised abdominal wall, to absorb any blood or fluid shedding from the incision or from the abdominal cavity behind the kidney. A piece of transparent pre-cut plastic was placed on top of the gauze pad in order to direct the blood flow from the kidney into the pad. Another one or two squares of gauze were laid at the base of the plastic platform and the renal vessels were occluded with a soft vascular clamp. A sagital heminephrectomy was performed and the entire distal half of the kidney was removed perpendicular to the renal vessels. The cut surface of the removed section of the kidney was blotted three times on a piece of filter paper to measure the surface area of the excision. Each of the three kidney blots were traced, to aid in surface area determination. The cut surface of the remaining kidney was blotted dry. The gelatin sponge was applied onto the cut surface of the kidney for 1 minute under pressure before releasing the renal clamp. The kidney was observed for incidence of bleeding for a period of one hour. When bleeding through the sponge occurred, the area of bleeding was gently blotted with gauze. Removal of the gelatin sponge from the bleeding surface resulted in resumption of bleeding, demonstrating that the cessation of bleeding was due to the gelatin sponge application. Renal Blood Loss was assessed by weighing the blood-soaked pads. At the end of the experiment the neck and axillary's incision sites were checked for hemorrhage and additional blood loss was estimated. Surviving animals were euthanized by $CO_2$ asphyxiation.

Example 1

The Relationship Between the Liquid Uptake and the Thickness and Appearance of the Gelatin Sponge after Vacuum Drying Procedure This experiment was aimed to determine the influence of the liquid uptake on the sponge thickness and appearance and to investigate the capability of different surfactant in increasing the liquid uptake. For this purpose, 7×5×1 (thickness) cm SPONGOSTAN™ sponges (Johnson & Johnson; cat No MS 0002) were cut to a size of 2.5×2.5×1 cm. These sponges (80-90 mg) were partially soaked in a plastic tray [3×3×0.2 (depth) cm] containing various liquids and volumes for 3 minutes (see Table 1 below). Hydration occurred as a result of capillary action. Afterwards, the sponges were dried in a vacuum oven as described above. The thickness of the sponges was measured following the drying procedure. The study design and the results are specified in Table 1 below.

TABLE 1

The Liquid Uptake and the Thickness of the Sponge Following Drying Procedure in the Different Formulations.

| Sponge No. | Liquid volume in the tray (µl) | Liquid | Liquid uptake (mg) | Thickness (mm) |
| --- | --- | --- | --- | --- |
| 1 | 500 | saline | 118.4 | 9 |
| 2 | 500 | distilled water + 0.1% NP40 | 457.8 | 3.7 |
| 3 | 200 | L9 + saline + 0.5% MB | 44 | 9 |
| 4 | 200 | L9 + saline ++ 0.01% NP40 + 0.5% MB | 163.9 | 7.2 |
| 5 | 600 | L9 + saline + 0.5% MB | 161.2 | 8.25 |
| 6 | 600 | L9 + saline + 0.5% MB | 164.7 | 8.25 |
| 7 | 600 | L9 + saline + 0.01% NP40 + 0.5% MB | 567.8 | 4.75 |

*L9- 20 mM Sodium Acetate, 0.5% w/w human albumin, and 2% w/w Mannitol; pH 6.9-7.1.
**NP40, a nonionic surfactant, was used to increases the liquid uptake of the cross-linked gelatin sponge. The surfactant was added to the solution to be absorbed.
***MB—Methylene Blue.

A. The Effect of Surfactant on the Liquid Uptake and the Thickness of the Sponge after Vacuum Drying. Sponges No. 1 and 2 were partially soaked in 500 µl saline or distilled water+0.1% NP40, respectively. Measurements of the sponge's liquid uptake reveled that partial soaking in fluids containing distilled water+0.1% NP40 resulted in high liquid absorption and in a significant decrease in the sponge's thickness upon vacuum drying as compared to saline soaked gelatin sponge (sponge No. 2 and No. 1; 457.8 mg liquid uptake and 3.7 mm thickness vs. 118.4 mg and 9 mm, respectively). The liquid uptake and the sponge's thickness in the different formulations are listed in Table 1.

Figure 1A:
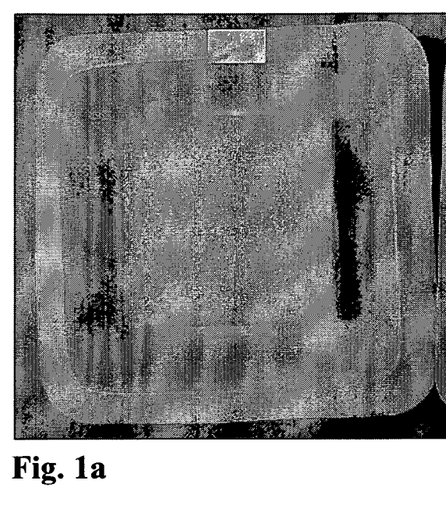
FIG. 1: shows a top view of a gelatin sponge partially soaked in 500 μl saline (A; sponge No. 1) as compared to a sponge partially soaked in 500 μl distilled water+0.1% NP40 (B; sponge No. 2) following the drying procedure. A sided view of the sponges is shown in C and D (sponge No. 1 and 2, respectively).
Figure 1B:
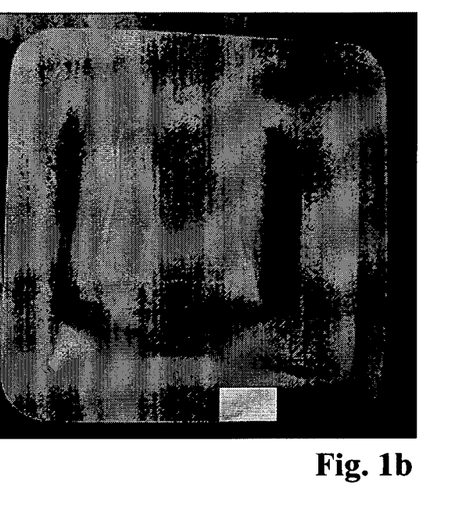
Figure 1C:
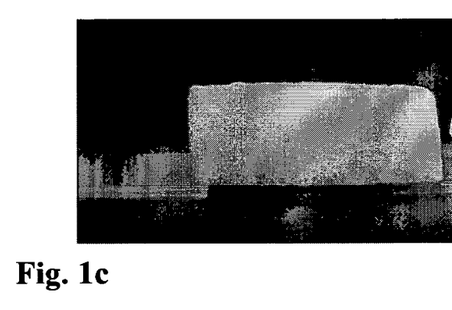
Figure 1D:
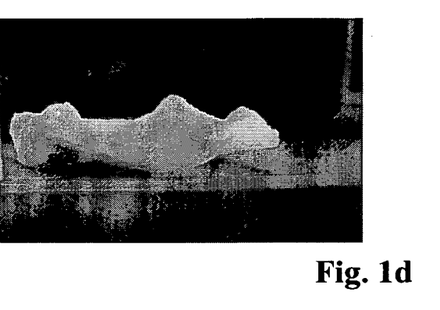

FIGS. 1A-B show a top view of a sponge partially soaked in saline (A; sponge No. 1) as compared to a sponge partially soaked in distilled water+0.1% NP40 (B; sponge No. 2) following the drying procedure. The results show that sponge B is distorted and shrunk, especially on the upper side where it absorbed liquid. In a sided view of the sponges it is evident that sponge 2 is thinner than sponge 1 (FIGS. 1D and C, respectively).

Figure 2A:
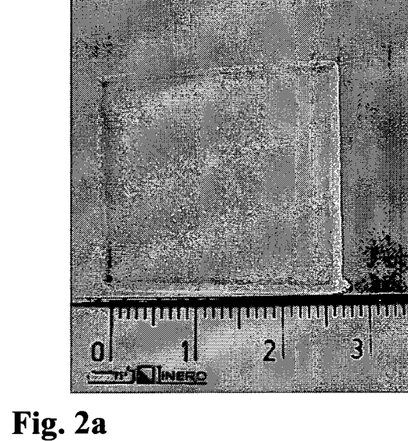
FIG. 2: shows a top view of gelatin sponges 6 and 7 partially soaked in 600 μl L9+saline+0.5% Methylene Blue (MB) and L9+saline+0.01% NP40+0.5% MB, respectively. A sided view of the sponges is shown in C and D (sponge No. 6 and 7, respectively).
Figure 2B:
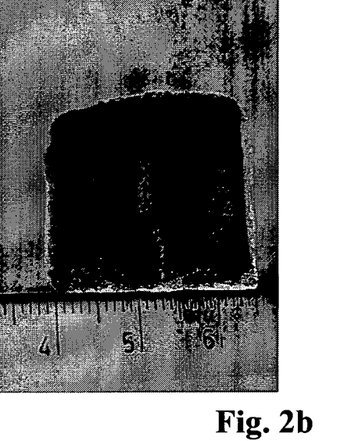
Figure 2C:
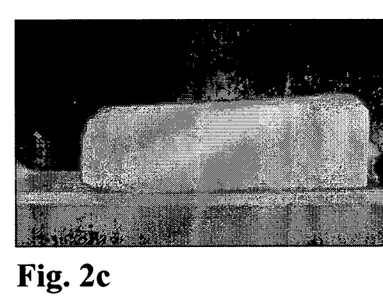
Figure 2D:
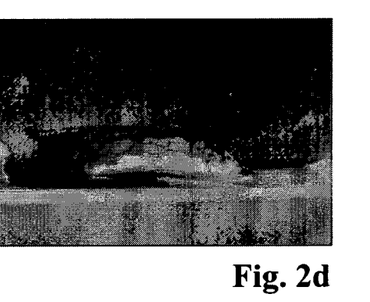

When comparing sponge 6 and 7 [600 µl of L9+saline+ 0.5% Methylene Blue (MB) or L9+saline+0.01% NP40+ 0.5% MB, respectively] the results show that even though an equal amount of liquid was added to both trays, sponge No. 7 absorbed more than 3 folds liquid compared to sponge No. 6. This is as a result of the presence of NP40 in the solution. As shown in the previous set of experiments, the high liquid uptake of sponge 7 resulted in a reduction in the sponge thickness upon vacuum drying (4.75 mm as compared to 8.25 mm of sponge 6). A top view of sponges 6 and 7 (FIGS. 2A-B, respectively) shows that sponge 7 is shrunken as compared to sponge 6. A side view shows that sponge 7 is thinner and distorted as compared to sponge 6 (FIGS. 2D-C, respectively). This is as a result of the high liquid uptake of the sponge which resulted in collapse of the sponge during drying.

Also, comparison of sponge No. 3 and 4 which were partially soaked in 200 µl L9+saline+0.5% MB and L9+saline+ 0.01% NP40+0.5% MB, respectively, shows that a surfactant increases the liquid uptake and consequently reduces the thickness of the sponge following vacuum drying (44 mg and 9 mm vs. 163.9 mg and 7.2 mm for sponge No. 3 and 4, respectively; Table 1).

The above results indicate that incorporation of surfactant, e.g. NP40, to the solution leads to a decrease in the liquid surface tension which subsequently results in an increase in the liquid uptake into the sponge. In addition, the increase in the liquid uptake results in a decrease in the sponge thickness upon vacuum drying. The liquid uptake was shown to be reversibly proportional to the sponge thickness.

B. The Effect of the Volume Solution during the Partial Soaking on the Liquid Uptake of the Sponge. In another set of experiments SPONGOSTAN™ sponges were partially soaked in a tray (the dimensions of the sponges and the trays are described above) containing 200 or 600 μl L9+saline+ 0.5% MB (sponges 3 and 5, respectively).

Figure 3A:
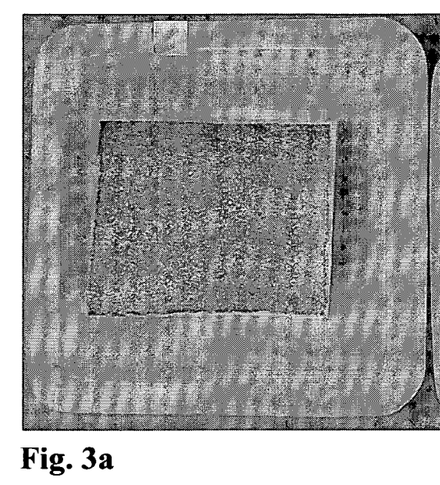
FIG. 3: shows a top view of gelatin sponges 3 and 5 partially soaked in 200 or 600 μl L9+saline+0.5% MB, respectively. A sided view of sponges 3 and 5 is shown in FIGS. 3C and D, respectively.
Figure 3B:
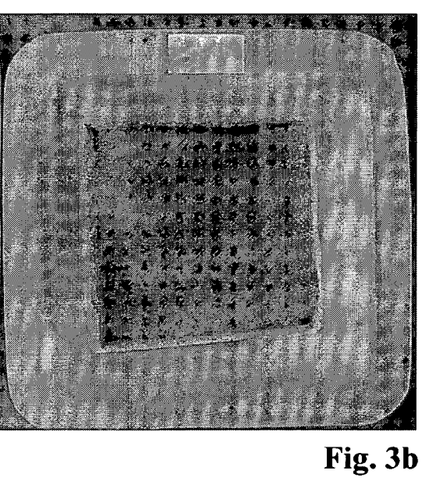

The results show that sponge 5 absorbed about 3.5 times more liquid as compared to sponge 3 (161.2 and 44 mg uptake for sponge, respectively). The high liquid absorbance of sponge 5 resulted in an intense coloring of the sponge as compared to sponge 5 (FIGS. 3A-B show a top view of sponges 3 and 5, respectively).

Figure 3C:
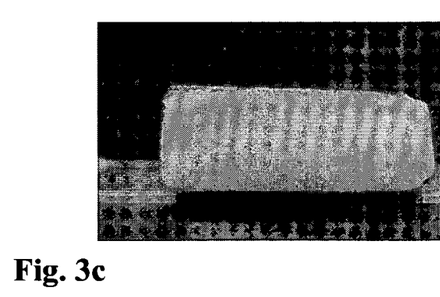
Figure 3D:
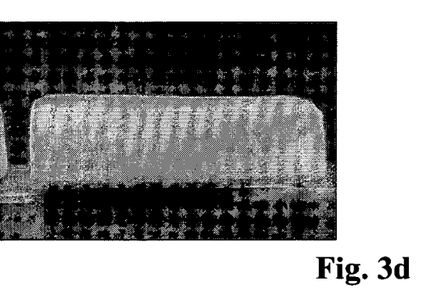

FIGS. 3C-D show sides view of sponges 3 and 5, respectively. Since the sponges absorbed relatively small volumes of liquid, minimal collapse occurred during vacuum drying in both volumes (9 and 8.25 mm, respectively).

The above shown results indicate that the volume present in the tray during soaking affects the liquid uptake of the sponge.

Example 2

The Effect of Ethanol on the Liquid Uptake of the Gelatin Sponge

The above example shows that the liquid uptake into the sponge by capillary action depends on the surface tension of the liquid and that addition of surfactant to the liquid to be absorbed facilitates the absorption ability of the sponge. These results were confirmed using ethanol and Gelitaspon™ (Gelita Medical; cat. No. GS010 Standard 10; size 80×50×10 mm). The sponges were cut to a size of 2.5×2.5×1 cm and placed in a plastic tray (3×3×0.2 cm pieces) containing various volumes of L9+0.1 M NaCl with or without 20% ethanol. The sponges were incubated for 15 minutes and weighed. The study design is specified in Table 2 below.

TABLE 2

Constitution of Test Groups.

| Liquid volume(μl) | Liquid |
|---|---|
| 250 | L9 + NaCl 0.1 M |
| 250 | L9 + NaCl 0.1 M + 20% ethanol |
| 400 | L9 + NaCl 0.1 M |
| 400 | L9 + NaCl 0.1 M + 20% ethanol |
| 550 | L9 + NaCl 0.1 M |
| 550 | L9 + NaCl 0.1 M + 20% ethanol |
| 700 | L9 + NaCl 0.1 M |
| 700 | L9 + NaCl 0.1 M + 20% ethanol |

Figure 4:
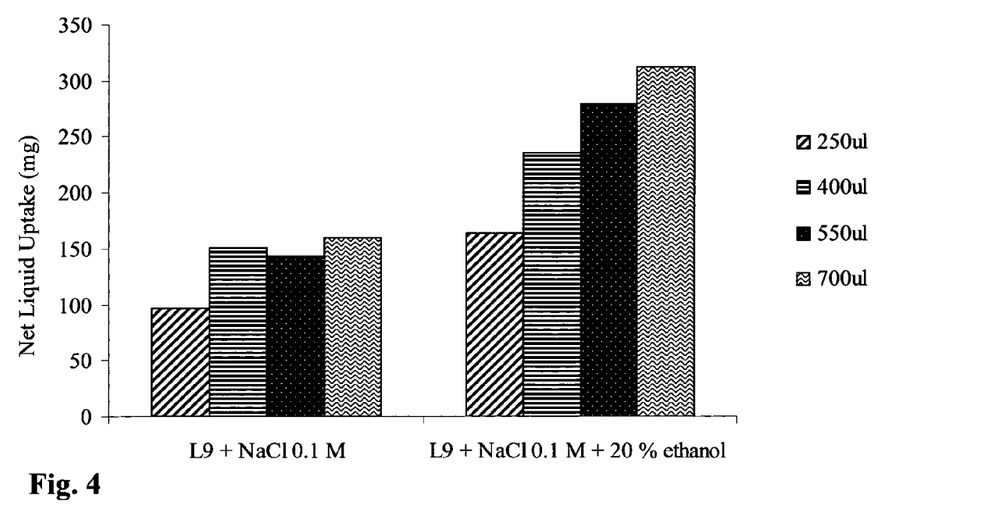
FIG. 4: shows the effect of ethanol on the liquid uptake of Gelitaspon™, a commercial gelatin sponge, in increasing volumes of L9 (20 mM Sodium Acetate, 0.5% w/w human albumin, 2% w/w Mannitol; pH 6.9-7.1)+0.1 M NaCl.

The results summarized in FIG. 4 corroborate the previous results and show that 20% ethanol increased the liquid uptake by Gelitaspon™ sponge.

Example 3

Effect of Ethanol on Thrombin Clotting Activity

The present example was aimed to determine the effect of ethanol addition on thrombin activity. For this purpose, 0.8 ml thrombin solution (1000 IU/ml; Omrix IL) was mixed with 0.2 ml 95% ethanol. The mixture was incubated at room temperature up to 60 minutes and thrombin activity was measured every 15 minutes. In the control group distilled water was used instead of ethanol. The following table summarizes the recovered thrombin activity in the formulation at various time points (Table 1):

TABLE 3

Recovered Thrombin Activity in the Various Time Points.

| Formulation | Time (min) | Thrombin Activity (IU/ml) | Recovered activity (%) |
|---|---|---|---|
| Thrombin + Ethanol | 15 | 677.6 | 83.34 |
| | 30 | 677.6 | 83.34 |
| | 45 | 635.2 | 78.13 |
| | 60 | 645.6 | 79.4 |
| Thrombin + Distilled water | 60 | 645.6 | 79.4 |

The recovered activity of thrombin+Distilled water was similar to the recovered activity of a formulation with ethanol, these findings suggest that 20% ethanol does not affect thrombin clotting activity.

Example 4

Kinetics of Liquid Absorption by Capillary Action into Various Sponges

Figure 5:
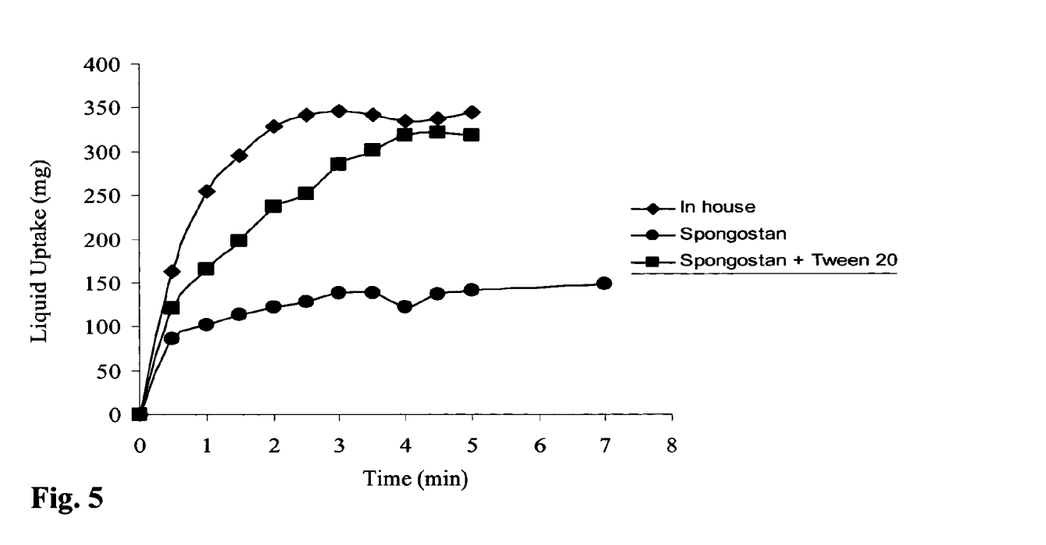
FIG. 5: shows the kinetics of liquid absorption by capillary action into SPONGOSTAN™ or in-house gelatin sponges (manufactured in Omrix IL) and the role of surfactant in the liquid uptake into the sponge.

This example illustrates the kinetics of liquid absorption by capillary action in two sponges of different origin and emphasizes the role of surfactant in the liquid uptake into the sponge. SPONGOSTAN™ weighing 80-90 mg or in-house sponges (manufactured in Omrix IL as described above) were placed in a plastic tray (3×3×0.2 cm) which contained 400 μl L9 buffer+0.1 M NaCl. In addition, SPONGOSTAN™ sponges were placed in another formulation which contained 400 μl L9 buffer+0.1 M NaCl+0.02% Tween 20. Liquid absorption was monitored by weighing the sponges at various time points. The results demonstrate that supplementation of the formulation with 0.02% Tween 20 significantly decreased the hydration time required to wet the sponge and increased the liquid uptake capability of the SPONGOSTAN™ sponges. Moreover, it is indicated that the in-house sponges absorb liquid more rapidly compared to the SPONGOSTAN™ sponges (FIG. 5).

Example 5

The Effect of the Liquid Uptake on the Sponge Thickness after Vacuum Drying

Figure 6:
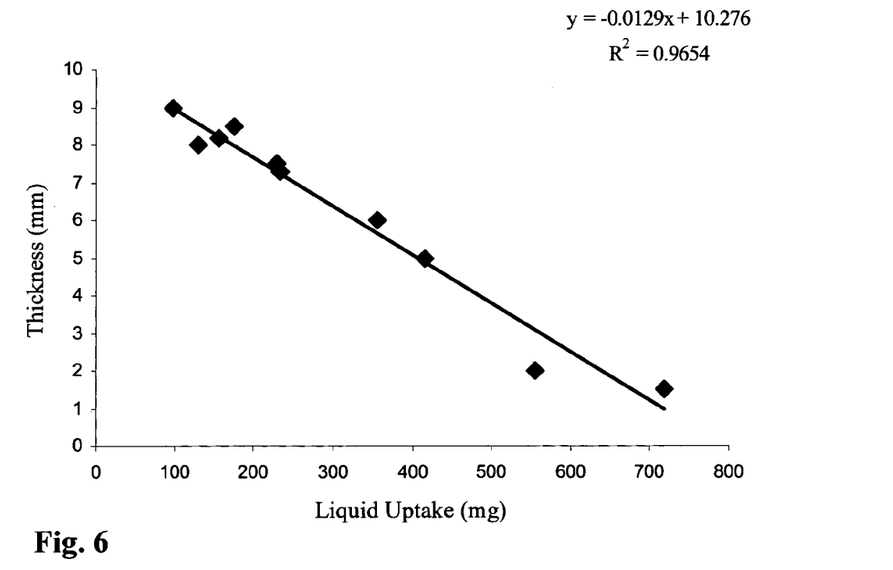
FIG. 6: shows the thickness of the vacuum dried SPONGOSTAN™ gelatin sponges plotted as a function of the liquid uptake of the sponge prior to drying.

It was shown that surfactant serves as a wetting agent which increases the liquid uptake of the sponge subsequently leading to a decrease in the sponge thickness upon vacuum drying. These results were verified in the following set of experiments. 2.5×2.5×1 cm SPONGOSTAN™ sponges [cut from 5×7×1 cm] were partially soaked in a tray [3×3×0.2 cm] containing various liquid volumes of L9+0.1 M NaCl. Following the wetting step the sponges were dried in a vacuum oven as specified above. The liquid volumes in the tray, the dried sponge weight, the liquid uptake and the thickness of the vacuum dried sponges are specified in Table 4 below. FIG. 6 shows the sponge thickness followed vacuum drying plotted against the liquid uptake of the sponge.

The results confirm the previous results and show that vacuum drying procedure results in collapse of the wetted sponge. Moreover, the results show that there is a reverse proportion between the liquid uptake and sponge thickness upon drying.

These results indicate the advantage of applying thrombin in a small amount of liquid to one surface of the gelatin sponge followed by drying, since by this procedure a sponge having a thin layer of thrombin on that surface and retaining the original characteristics of the sponge (height, texture and appearance) can be obtained.

Example 6

Figure 7:
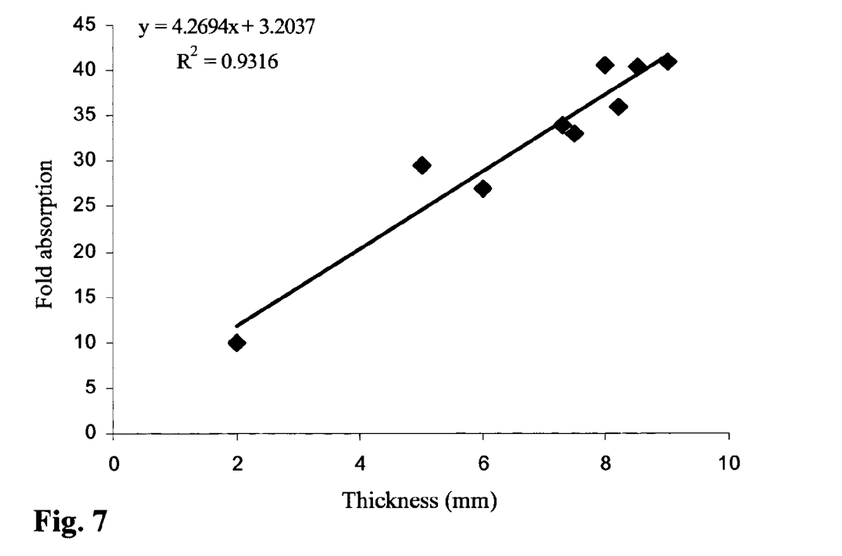
FIG. 7: shows the SPONGOSTAN™ gelatin sponges water fold absorption plotted as a function of the thickness of the vacuum dried sponges.

The Effect of the Sponge Thickness after Vacuum Drying Procedure on the Water Absorption Ability of the Sponge In order to check the liquid absorption ability of the vacuum-dried sponges, the above mentioned vacuum dried sponges (from example 5) were immersed in distilled water for 2 minutes according to the US Pharmacopeia (USP) and weighed. The thickness of the sponges, the vacuum dried sponge's weight and the water absorption are listed in Table 4 below. The water absorption ability of the sponge was calculated according to the following formula: (Wet weight−dry weight after vacuum)/dry weight after vacuum. The sponge fold absorption plotted against the thickness is shown in FIG. 7. The results indicate that the ability of the sponge to absorb fluids is directly proportional to the thickness of the sponge following the vacuum drying procedure, i.e., thin sponges absorb less fluid than thick sponges.

According to the US Pharmacopeia absorbable gelatin sponges should absorb not less than 35 times their weight of water. In order to meet the pharmacopeia demand, SPONGOSTAN™ sponges should retain a thickness of equal or more than 7.44 mm, i.e. these sponges should loss not more than 25% from their initial height during the drying procedure. Moreover, in order to obtain a thickness of equal or more than 7.44 mm the liquid uptake of SPONGOSTAN™ sponges should be equal or less than 219 µl (according to example 5; FIG. 6).

TABLE 4

The Effect of the Liquid Uptake on the Sponge Thickness after Vacuum Drying and the Water Absorption Ability of the Vacuum-Dried-Sponges.

| Liquid Volume in the Tray (µl) | Dry Sponge Weight (mg) | Liquid Uptake (mg) | Thickness after Vacuum (mm) | Dry Weight after Vacuum (mg) | Net Water absorption of final product (mg) | Water Absorption ability* |
|---|---|---|---|---|---|---|
| 400 | 87.7 | 99.4 | 9 | 95.1 | 3892.1 | 41 |
| 250 | 93 | 156.4 | 8.2 | 101.2 | 3665.9 | 36 |
| 400 | 90.7 | 233 | 7.3 | 100.5 | 3450.6 | 34 |
| 400 | 87.1 | 229.3 | 7.5 | 97.2 | 3208.6 | 33 |
| 550 | 93.3 | 415.6 | 5 | 112 | 3306.7 | 29.5 |
| 550 | 92.4 | 355.5 | 6 | 111.7 | 3032.1 | 27 |
| 750 | 93.8 | 719.4 | 1.5 | 145.3 | 2739.6 | 18.9 |
| 700 | 84.2 | 555.1 | 2 | 130.4 | 1304 | 10 |
| 400 | 79.4 | 131.4 | 8 | 82.1 | 3369.2 | 40.5 |
| 400 | 80 | 176.6 | 8.5 | 87.8 | 3567 | 40.4 |

*The water absorption ability of the sponge was calculated as follows (wet weight − dry weight after vacuum)/dry weight after vacuum.

Example 7

Comparison Between Lyophilization and Vacuum Drying Procedure on the Thickness of the Sponge The drying procedure of the gelatin sponge should be appropriated for a material containing an active protein ingredient i.e., the drying procedure should not denature the proteins in the sponge or render them inactive.

In the following example the effect of lyophilization and vacuum drying procedures, which do not denature the active ingredients of the gelatin sponge, on the thickness of the sponge was evaluated. The experiment was carried out using two different gelatin sponges, a commercial sponge (5×7×1 cm SPONGOSTAN™ sponge) and an in-house sponge (manufactured as described above).

Both sponges were cut to 2.5×2.5×1 cm (80-90 mg for SPONGOSTAN™ and in-house sponges) and placed in a plastic tray (3×3×0.2 cm) containing increasing volumes (200-750 µl) of L9+0.1 M NaCl for 3 minutes. The sponge's weight after the wetting step was measured and the net liquid uptake was calculated.

Afterwards, SPONGOSTAN™ was dried either in a vacuum oven or in lyophilization (as described above) and the in house sponge was dried by a vacuum oven. The thickness of the sponges was measured following the drying procedure.

Figure 8:
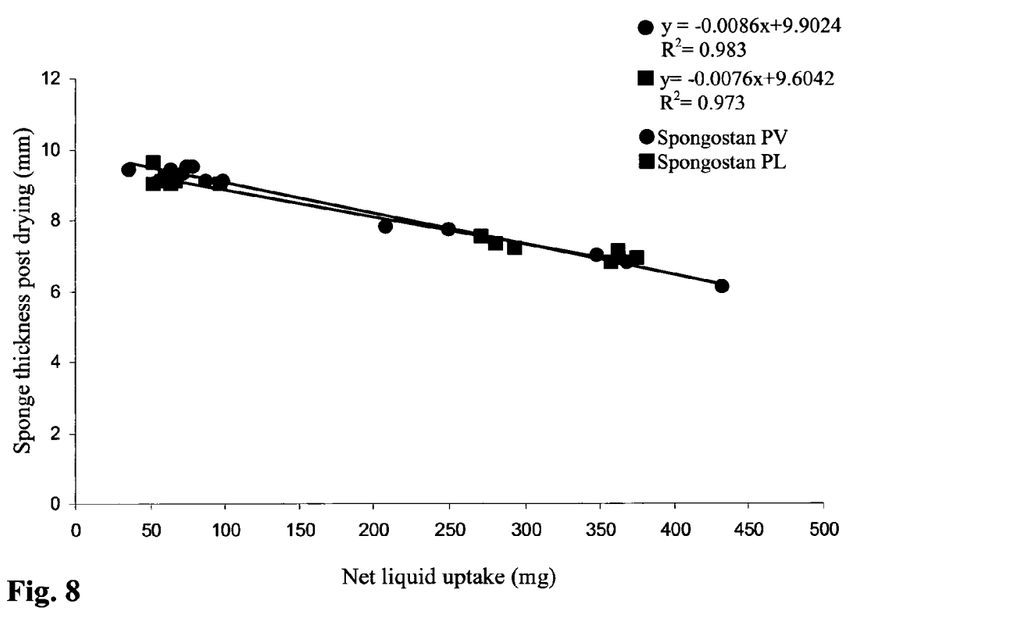
FIG. 8: shows the inverse relationship between the thickness of the SPONGOSTAN™ sponges after the drying procedure and the net liquid uptake of the sponge prior to drying procedure. PV—partially soaked sponges followed by vacuum drying; PL—partially soaked sponges followed by lyophilization drying procedure.

FIG. 8 shows the inverse relationship between the thickness of the commercial sponge (SPONGOSTAN™) after the drying procedure and the net liquid uptake. PV—partially soaked sponges followed by vacuum drying; PL—partially soaked sponges followed by lyophilization drying procedure.

Figures 9A, 9B:
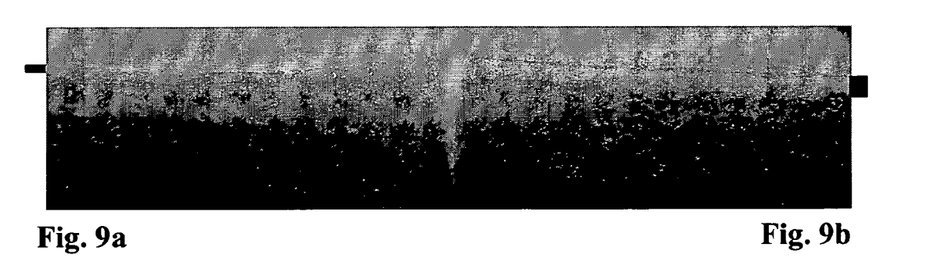
FIG. 9: shows the thickness of the applied active ingredient layer within the vacuum-dried gelatin sponges (A, C) and the lyophilized-dried gelatin sponges (B, D).
Figures 9C, 9D:
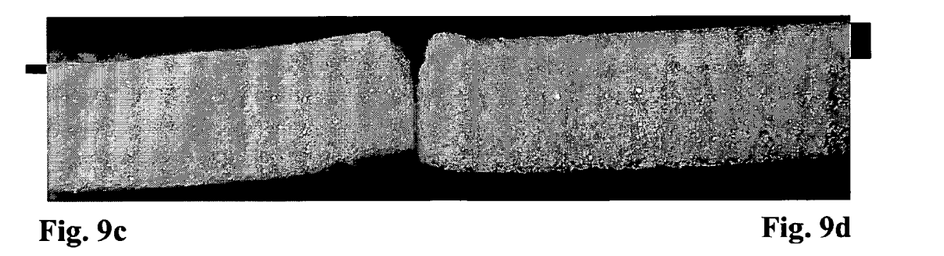

The results show that an increase in the net liquid uptake resulted in a decrease in thickness of the sponge in a similar extent in both lyophilization and vacuum drying procedure. However, when comparing the thickness of the layer of the applied active ingredient, the results show that drying in vacuum (FIG. 9A, C) results in a thinner layer as compared to lyophilization drying procedure (FIG. 9B, D). The dried top layer of the vacuum dried sponge was 5.8-8.3% of the overall thickness of the sponge as compared to 12.5-24% in the lyophilized sponge. The thickness layer of the applied material is marked in a black square at the top of each Figure.

Figure 10:
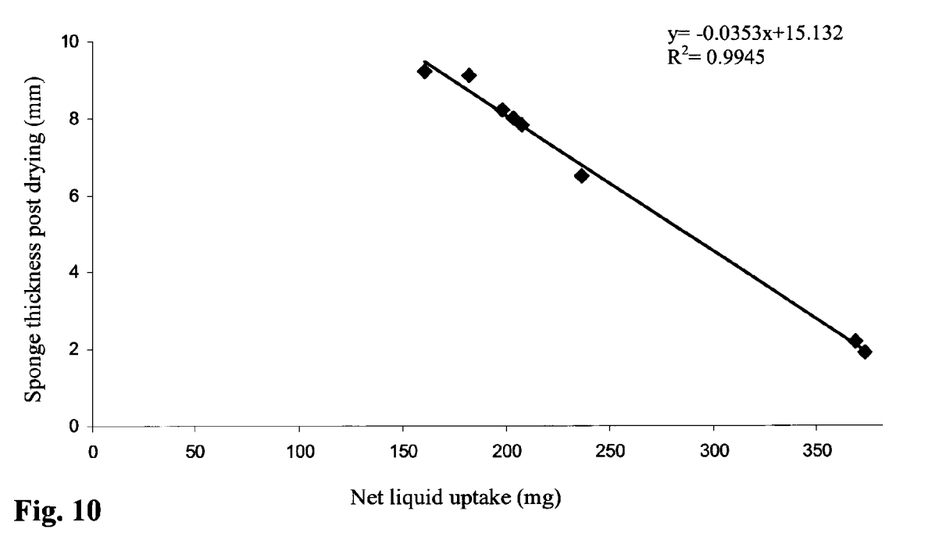
FIG. 10: shows the relationship between the sponge thickness after drying and the net liquid uptake of the in-house sponge.

The results of the relationship between the sponge thickness after drying and the net liquid uptake of the in-house sponge are presented in FIG. 10. These results are in line with the previous results which indicate that there is an inverse relationship between the liquid uptake and the sponge thickness following the drying procedure.

Example 8

Release of the Active Ingredient from Different Gelatin Sponges

The following example was preformed in order to determine the release of the active material from the gelatin sponge and to assess the in-vivo performance of the sponge. For this purpose, 2.5×2.5×1 cm SPONGOSTAN™ gelatin sponges were completely or partially soaked as specified below. For complete soaked sponges: 2 ml thrombin solution (1000 IU/ml) was added to 20 ml L9 buffer to obtain 90 IU/ml solution. The sponges were wetted, kneaded and soaked in this solution for about 1 min and absorbed approximately 2.5 ml which correspond to 35 IU/cm$^2$ (225 IU/inch$^2$). The partial soaked sponges were immersed in a 3×3×0.2 cm plastic tray containing 400 µl thrombin solution (1600 IU/ml) for about three min. The solution was absorbed by capillary action. In this way the sponge absorbs an average 140 mg liquid which corresponds to 225 IU/inch$^2$. Afterwards, the completely soaked sponges were dried in lyophilization and the partially soaked sponges were dried in a vacuum oven (both drying procedures were carried out as specified above).

Thrombin release from the sponge was tested by measuring thrombin clotting activity at various time points as specified above.

Figure 11:
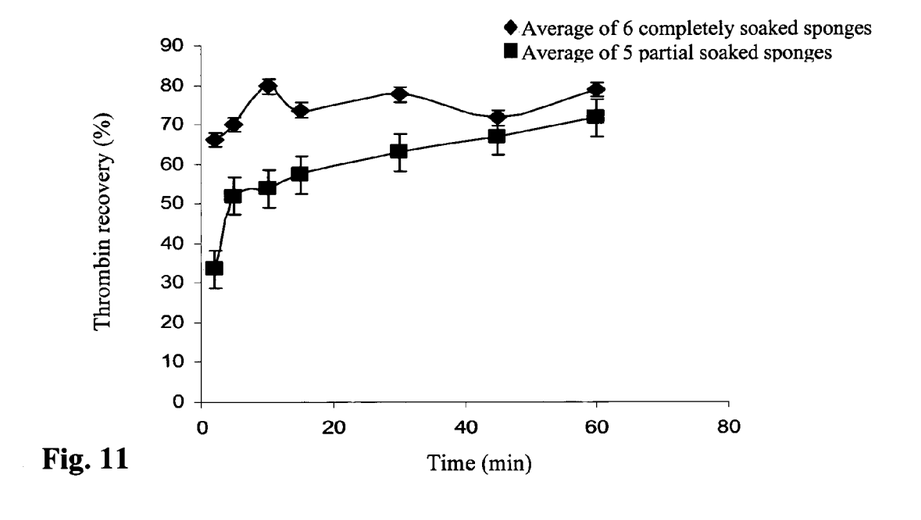
FIG. 11: shows the release of the active ingredient from complete soaked SPONGOSTAN™ sponges dried by lyophilization compared to partially soaked sponges dried in a vacuum oven.

The findings summarized in FIG. 11 suggest that complete soaking followed by lyophilization releases thrombin faster than a partially soaked sponge dried in a vacuum oven which in the thrombin was gradually released. Furthermore, the results show that at the end of the testing both sponges had similar recovered activity indicating that the partial soaked sponge dried in a vacuum oven preserves the thrombin activity.

An in vivo evaluation of the haemostatic characteristics of the two gelatin sponges [complete soaking followed by lyophilization drying procedure (A) and partially soaked sponge dried in a vacuum oven (B)] was done using the Rat Kidney Hemorrhage Model as described above. The blood loss using the different sponges is presented in Table 5.

TABLE 5

Blood Loss in Rat Kidney Model Using Different Gelatin Sponges.

| Sponge type | Blood Loss (g) | Average Blood Loss (g) |
|---|---|---|
| Complete soaking + lyophilization (A) | 1.39, 4.08, 6.54, 0, 4.44, 1.7 | 3.02 ± 2.9 |
| Partial soaking + vacuum drying (B) | 0, 0.23, 2.82, 0.11, 5.45, 0.97 | 1.59 ± 2.16 |

* No statistical difference was found between the two groups at a significance level of 0.05 using t-TEST analysis.
* All experiments were preformed with SPONGOSTAN ™ Gelatin sponge consisting of 35 IU/cm² thrombin.

The results show that both sponges were equally efficient in preventing blood loss when applied to a bleeding surface. However, vacuum drying procedure is superior to lyophilization drying procedure when taking into account the following advantages: cheap manufacturing, shorter preparation time and substantially preservation of the original porous structure and mechanical properties of the sponge.

Example 9

Haemostatic Efficacy Achieved by a Gelatin Sponge Prepared by Partial Soaking and Vacuum Drying This example evaluates the haemostatic characteristics of a ready-to-use gelatin sponge prepared by partial soaking and vacuum drying using the Rat Kidney Hemorrhage Model as described above.

The gelatin sponges were prepared as described above and dried in a vacuum oven as indicated above (Example 8; partial soaked sponges). The total amount of thrombin applied to the wound-contacting surface of the sponge was 35 IU/cm² thrombin The following Table summarizes the blood loss using the ready-to-use gelatin sponge (Table 6):

TABLE 6

Blood Loss in Rat Kidney Model Using Different Gelatin Sponge Compositions.

| Sponge composition | Blood Loss (g) | Average Blood Loss (g) |
|---|---|---|
| CONTROL SPONGE (A) | 2.84, 6.19, 6.2, 5.15 | 5.1 ± 1.58 |
| SPONGE + Thrombin (B) | No bleeding, 0.23, 2.82, 0.11, 5.45, 0.97 | 1.6 ± 2.16 |

* Group A vs. group B p = 0.0091 using t-TEST analysis.
* All experiments were preformed with SPONGOSTAN ™ Gelatin sponge consisting of 35 IU/cm² thrombin.

The above data demonstrates that gelatin sponge with thrombin (composition B) is more effective in preventing blood loss than control gelatin sponge (composition A) i.e., blood loss was significantly reduced using a gelatin sponge which comprises a thin layer of thrombin on one surface of the sponge.

What is claimed is:

1. A method for manufacturing an improved cross-linked gelatin sponge comprising a protein or peptide active ingredient comprising the steps of:
    a) providing a cross-linked gelatin sponge having at least one surface;
    b) homogenously applying an aqueous liquid comprising a protein or peptide active ingredient to said at least one surface of said sponge, wherein the volume of the liquid intake into said surface of said sponge is equal to or less than 5% of the volume of the sponge in a); and
    c) drying the sponge by a drying step selected from the group consisting of thermal drying, vacuum drying and freeze drying,
    thereby obtaining a flexible, dry cross linked gelatin sponge comprising a stable layer of protein or peptide active ingredient on at least one surface of the sponge.

2. The method according to claim 1, wherein said liquid applying step is carried out in a single stage.

3. The method according to claim 1, wherein epsilon aminocaproic acid is absent from said liquid.

4. The method according to any one of claims 1 to 3, wherein said liquid applying step is carried out by using a roller.

5. The method according to claim 4, wherein said liquid applying step comprises the steps of:
    a) providing a rotating roller having an external surface, wherein at least a portion of said external surface is in contact with a reservoir comprising said liquid;
    b) rotating the roller to cover said external surface with said liquid;
    c) contacting said external surface of the roller with said at least one surface of said sponge; and
    d) moving said external surface of the roller and said at least one surface of said sponge relative with one another;
    thereby depositing said liquid onto said at least one surface of said sponge.

6. The method according to claim 5, wherein said external surface includes a plurality of hollowed spaces capable of holding said liquid.

7. The method according to any one of claims 1 to 3, wherein said liquid applying step is carried out by using a liquid dispenser.

8. The method according to claim 7, wherein said liquid applying step is carried out by using the PipeJet™-technology.

9. The method according to any one of claims 1 to 3, wherein the thickness and the flexibility of the dried sponge are substantially similar to those of the sponge in a).

10. The method according to claim 9, wherein at least 75% of the thickness of the sponge in a) is retained.

11. The method according to any one of claims 1 to 3, wherein the thickness of said layer is equal to or less than 24% of the overall thickness of the sponge following the drying step.

12. The method according to any one of claims 1 to 3, wherein said drying step is carried out by a process selected from the group consisting of: vacuum oven, freeze-drying, and air drying.

13. The method according to claim 12, wherein said drying step is carried out by vacuum oven.

14. The method according to any one of claims 1 to 3, wherein said active ingredient comprises thrombin.

15. The method according to any one of claims 1 to 3, wherein the thrombin activity in said liquid is in the range of from about 2 to about 15,000 IU/ml, in the range of from about 2 to about 4,000 IU/ml, or in the range of from about 4,000 to about 10,000 IU/ml.

* * * * *